United States Patent [19]

Chow

[11] Patent Number: 5,353,812
[45] Date of Patent: Oct. 11, 1994

[54] TRIGGER FINGER RELEASE SURGICAL METHOD

[76] Inventor: James C. Y. Chow, 3001 Caroline St., Mount Vernon, Ill. 62864

[21] Appl. No.: 135,453

[22] Filed: Oct. 12, 1993

[51] Int. Cl.⁵ ............................................. A61B 17/00
[52] U.S. Cl. ..................................... 128/898; 606/167
[58] Field of Search ................. 128/897, 898; 623/57, 623/64, 66; 606/167

[56] References Cited

U.S. PATENT DOCUMENTS 4,962,770 10/1990 Agee et al. ........................... 128/898

Primary Examiner—Lee S. Cohen
Assistant Examiner—Samuel Gilbert
Attorney, Agent, or Firm—Polster, Lieder, Woodruff & Lucchesi

[57] ABSTRACT

A method of performing trigger finger release surgery. A flexor tendon (T) passes through the palm (P) of a person's hand (H) to a finger (F) or thumb (B). For a person suffering from trigger finger, the path (1) of the impaired tendon is first identified. Constriction of a protective sheath (E) around the flexor tendon causes the trigger finger condition. A puncture site is identified for insertion of one end of a hollow surgical instrument (1) into the palm. The surgical instrument is pushed through the palm of the hand so that a first puncture hole (U) is made where the instrument enters into the palm, and a second puncture hold (U') where the instrument exits from the palm. The instrument is routed through the palm such that the path (8) of the instrument passes through the sheath. The surgical instrument is left in place and an arthroscope (9) and a surgical knife (11) are inserted into respective ends of the instrument. The surgeon views the surgical site through a monitor (10) while cutting the sheath with the knife. The arthroscope, knife, and surgical instrument are then withdrawn. The size of the surgical instrument is such that after its withdrawal, the puncture holes made in the hand do not require stitches to close them. As the wounds heal, no scars are formed.

20 Claims, 5 Drawing Sheets

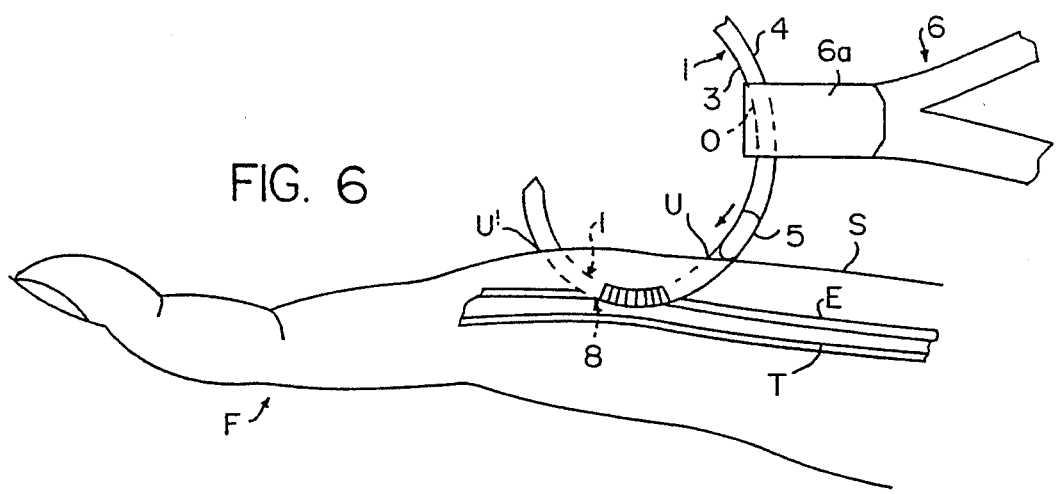
FIG. 6
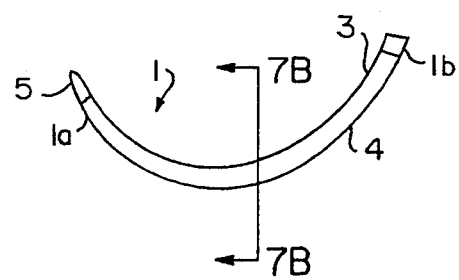
FIG. 7A
FIG. 7B
FIG. 7C
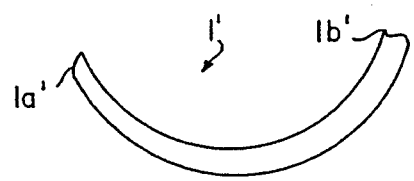
FIG. 7D
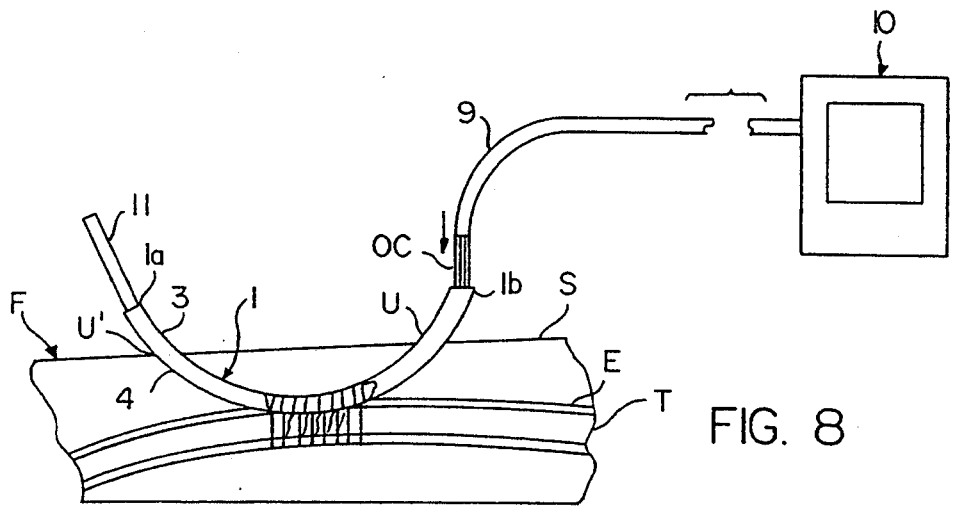
FIG. 8

TRIGGER FINGER RELEASE SURGICAL METHOD

BACKGROUND OF THE INVENTION

This invention relates to arthroscopic surgical procedures and, more particularly, to an improved procedure to perform trigger finger release and trigger thumb release.

Trigger finger or trigger thumb is a condition which typically effects the middle aged. It manifests itself as an involuntary movement of a finger or thumb in response to a sensed pressure in the palm of the hand. Although the condition may be congenital, it is seldom found in children over the age of two. If combined with a collagen disease which attacks the connective tissue in the hand, several fingers of a person's hand may be involved. The condition most often effects the middle finger or ring finger; although, as the name implies, the thumb is also often involved. If a nodule is formed, or a fusiform (spindle-like) swelling occurs, a restriction, or narrowing, or stenosis of the flexor tendon results. This narrowing occurs adjacent the sheath or theca covering the tendon at the distal crease in the palm of the hand. The nodule usually appears at the point where the tendon enters the proximal annulus at the level of the metacarpophalangeal joint. Applying pressure to the nodule, such as by palpatating it, causes the nodule to move with the tendon. If the thumb is involved, the interphalangeal joint will be the one that appears to snap or lock, even though the constriction is, as noted, associated with the metacarpophangeal joint.

Sectioning of the annulus through a surgical procedure may relieve the triggering. In some instances, a partially lacerated flexor tendon will heal with a nodule large enough that there may be a recurrence of the triggering. Or, if the patient is rheumatoid, there may be complications. However, the problem is one which lends itself to a surgical solution. One problem with current surgical techniques is that they require a lengthy incision to be made in the palm of the hand to facilitate insertion of a surgical knife or scissors used to cut the sheath surrounding the flexor tendon and relieve the constriction. Once the knife or scissors is removed, stitches are required to close the wound. This results in scarring. Arthroscopic surgical apparatus for releasing trigger finger is described in my co-pending U.S. patent application Ser. No. 07/135,462, filed Dec. 10, 1993.

SUMMARY OF THE INVENTION

Among the several objects of the present invention may be noted the provision of a endoscopic surgical method for use in relieving a trigger finger or trigger thumb condition in a patient; the provision of such an endoscopic procedure in which a reference point at the center of the thenar and lesser thenar muscles is first identified; the provision of such an endoscopic procedure to determine the route of the flexor tendon going to each finger and thumb using the reference point and to locate an appropriate incision site; the provision of such an endoscopic procedure to puncture the skin in the palm at first and second spaced sites to allow appropriate endoscopic surgical instruments to be inserted into the hand and employed to release a distal palm pulley causing the trigger finger; the provision of such an endoscopic procedure in which the incisions are sufficiently small that after completion of the surgery no sutures are required to close the puncture hole so after healing no scars are formed in the palm of the hand; the provision of such an endoscopic procedure to be performed by a surgeon as readily as previous surgical procedures used to effect similar repairs; and, the provision of a surgical method which can be performed at any convenient location such as the surgeon's office, a clinic, or a hospital and requires only an attending physician and a surgical nurse or aide.

In accordance with the invention, generally stated, a method of performing trigger finger release surgery is disclosed. A flexor tendon for each finger and thumb of a hand is routed through the palm of the hand. Constriction of a protective sheath around a flexor tendon causes the trigger finger condition. According to the method, the routing path of the flexor tendon to the particular finger is first identified. A puncture site is then located along the path for insertion of one end of a hollow surgical instrument into the palm. A first puncture hole is made in the hand at the site by inserting one end of the instrument through the skin. The leading end of the instrument is then pushed back through the skin. This creates a second puncture hold at the exit site. The surgical instrument is routed through the hand such that its path passes through the sheath. The surgical instrument is left in place and a surgical knife by which the sheath is to be cut to relieve the trigger finger condition is inserted into the instrument. The knife is used to cut the sheath and release the trigger finger. After this is done, the knife is removed from the instrument and the instrument is withdrawn. The size of the instrument is such that after its withdrawal, the first and second puncture wounds do not require stitches to close them. And, as the wounds heal, no scars are formed. Other objects and features will be in part apparent and in part pointed out hereinafter.

BRIEF DESCRIPTION OF THE DRAWINGS

FIG. 6 is a simplified cross-sectional view of the hand illustrating one step in practicing the method;

FIG. 7A is an elevational view of a slotted cannula used in the surgery, FIG. 7B is a sectional view of the cannula taken along line 7B–7B in FIG. 7A, FIG. 7C is a plan view of the cannula, and FIG. 7D illustrates an alternate embodiment of the cannula;

FIG. 8 illustrates a second step in the surgery;

Corresponding reference characters indicate corresponding parts throughout the drawings.

DESCRIPTION OF A PREFERRED EMBODIMENT

Figure 1:
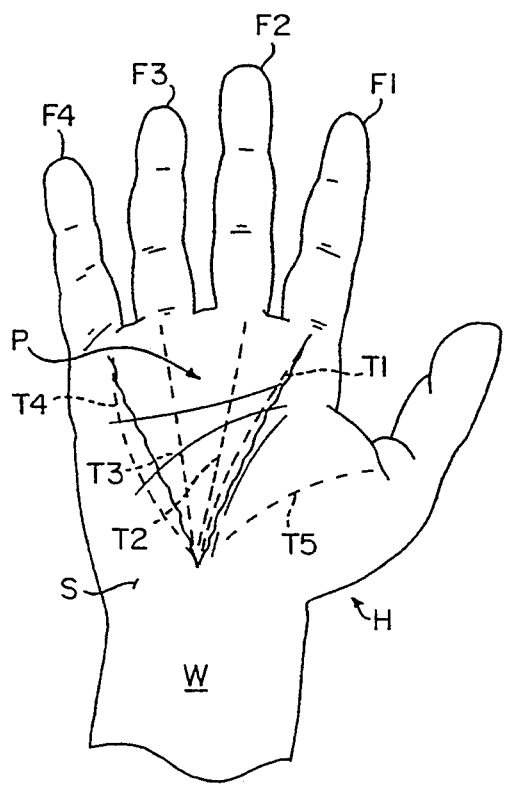
FIG. 1 is a view of the palm side of a hand with flexor tendons for various of the fingers being indicated.
Figure 3:
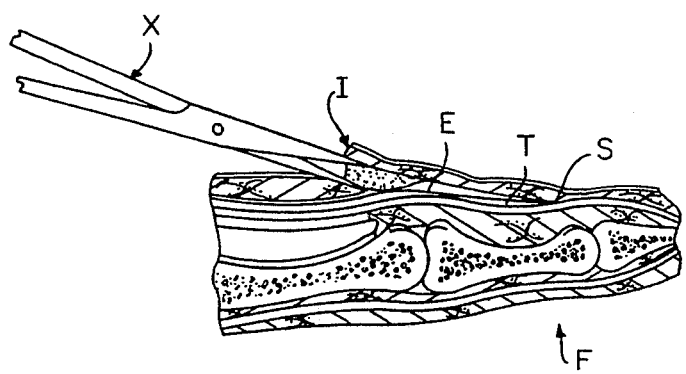
FIG. 3 is a partial cross-sectional view of the hand illustrating the surgical procedure.

Referring to the drawings, FIG. 1 illustrates a hand H having fingers F1-F4 and a thumb B. As indicated by the dashed lines in FIG. 1, tendons commonly referred to as flexor tendons T1-T5 extend beneath the skin S on the palm P of the hand to each of the fingers and thumb. As seen in FIG. 3, each flexor tendon is surrounded by a protective sheath E. Movement of the tendons produces flexure of the fingers as the hand is manipulated. A condition known as trigger finger occurs when the sheath is constricted about the tendon. This constriction results from formation of nodules (not shown) among other causes.

Figure 2:
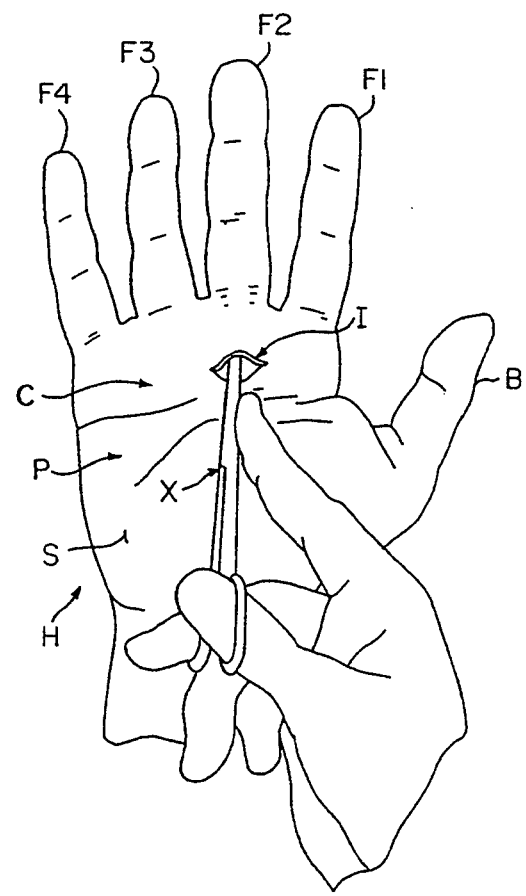
FIG. 2 shows the hand with a conventional trigger finger release procedure being performed on one of the flexor tendons.
Figure 4:
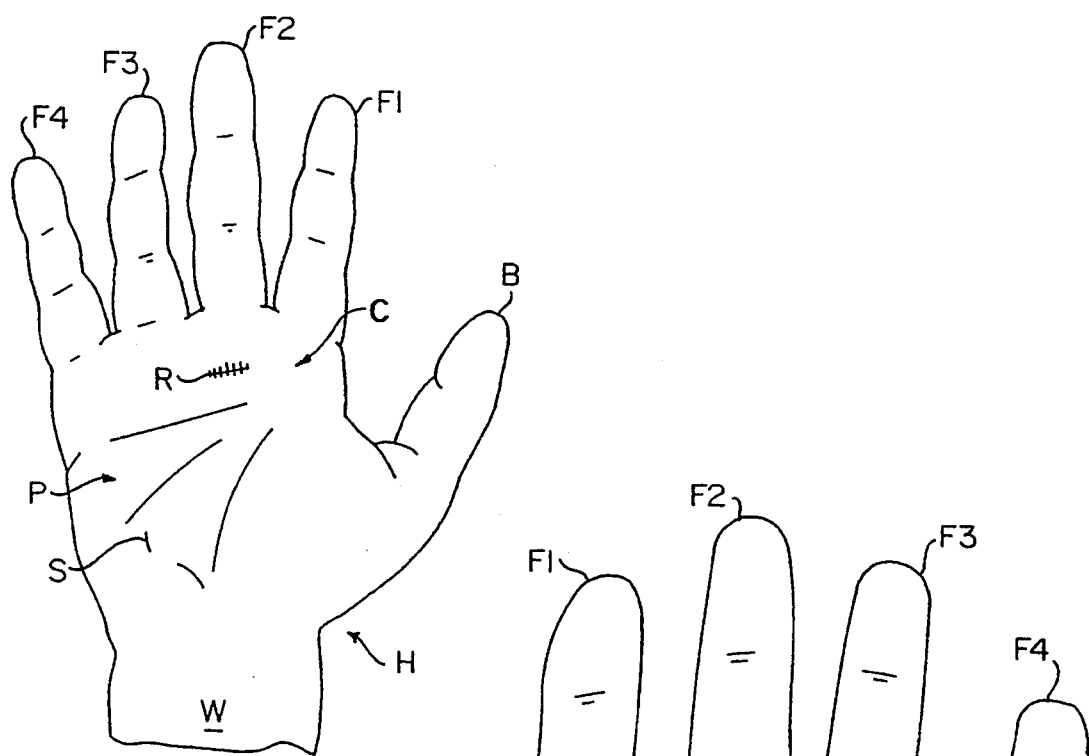
FIG. 4 is a view of the hand after the surgery has been performed.

FIGS. 2 and 3 illustrate a conventional surgical technique and surgical instruments for use in repairing trigger finger. As shown in FIG. 2, an incision I is made in the palm of the hand adjacent the distal crease C in the palm. A scissors X, scalpel, or other cutting instrument is inserted through the incision. The cutting instrument is used to cut open the sheath or annulus covering the tendon. This relieves the constriction. After withdrawal of the cutting instrument, the incision is sewn shut. After healing, the person on whom the operation is performed is left with a scar R such as shown in FIG. 4. While presence of a scar does not necessarily effect the person's ability to use their hand, it is unsightly, and can be avoided.

Referring now to FIGS. 5-9, surgical apparatus as described in my U.S. patent application Ser. No. 08/135,462, filed Dec. 10, 1993, is for performing trigger finger release surgery. The advantage of my surgical procedure over that shown in FIGS. 2 and 3 is that while it is easy to perform, it allows the surgeon a better view of the surgical site, enables the surgeon to make a more precise cut of the pulley or sheath surrounding the tendon; and, after the surgery is completed, leaves no residual, unsightly scars.

Figure 5:
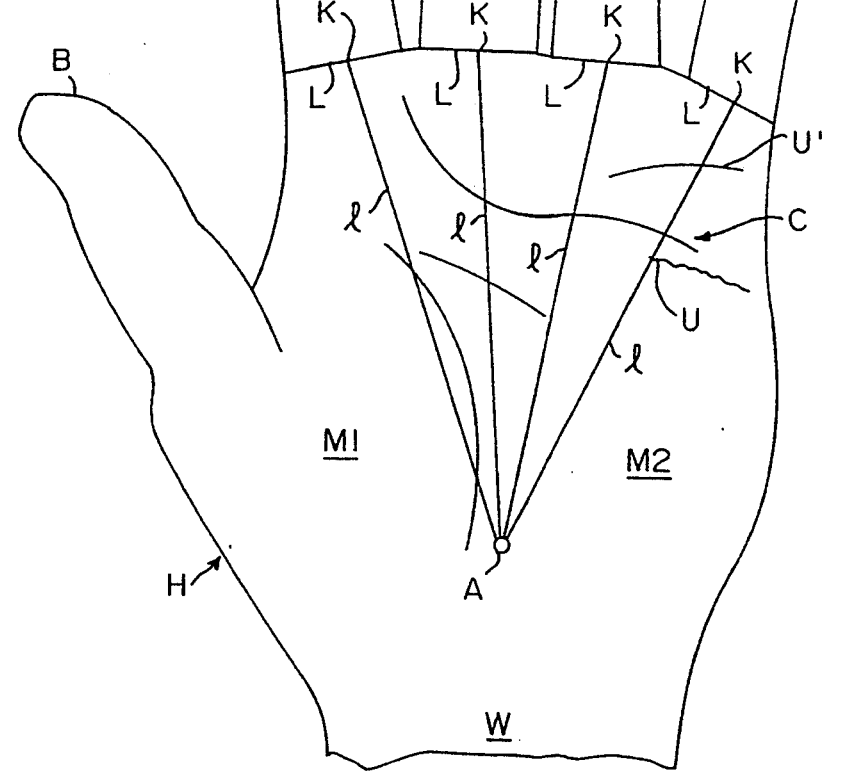
FIG. 5 is a view of a hand illustrating how flexor tendons goings to each finger are located in accordance with the surgical method of the present invention.

The first step in performing the surgery is to identify the path of the flexor tendon to the effected finger. In FIG. 5, this is shown to be done by first locating a point A at the base of the palm where the hand joins with the wrist W. This reference point is found to be at the center of the thenar and lesser thenar muscles M1 and M2 respectively. Next, a line L is drawn across the base of the finger and the midpoint of this line marked as indicated at K. Finally, a line 1 is drawn from point A to point K. The flexor tendon T for the respective finger generally follows a path through the palm corresponding to the line 1 drawn on the skin of the palm.

The next step in the procedure is to locate along line 1 a puncture site U for inserting a surgical instrument 1 of the invention into the palm. Typically, the constriction in the sheath is found to be caused by a nodule. And, this nodule usually occurs where the flexor tendon crosses the distal crease C in the palm of the hand. Therefor, puncture site U will usually be adjacent the distal crease. As seen in FIG. 5, site U is toward the reference point A side of the distal crease.

Referring to FIGS. 6, and 7A-7C, a surgical instrument 1 of the present invention is shown to be a hollow, curved cannula. The cannula is generally circular in cross-section and is, for example, only 1.5 mm.—2.5 mm in diameter. Further, the cannula has an arcuate or concave profile with the distance from one end of the cannula to the other being, for example, 25 mm. Further, the cannula has longitudinally extending slot 2 formed along the inner curved surface 3 of the cannula. Thus, as seen in FIG. 7B, the cannula has a general C-shape when viewed in cross-section. Slot 2 extends the entire length of the cannula. The outer curved surface 4 of the cannula is solid along the length of the instrument. As shown in FIG. 6, a trocar 5 is inserted in one end (the forward end) of the cannula. After fitting the trocar in the cannula, the surgeon siezes the cannula in a holder 6 and inserts the trocar end of the cannula into the palm of the hand at the selected site U. The surgeon then pushes the trocar end of the cannula through the palm of the hand until it comes back out through the skin making a second puncture hole U' in the skin at the exit site. The path 8 described by the cannula as it is pushed through the palm of the patient's hand passes through the sheath surrounding the flexor tendon.

Figure 12:
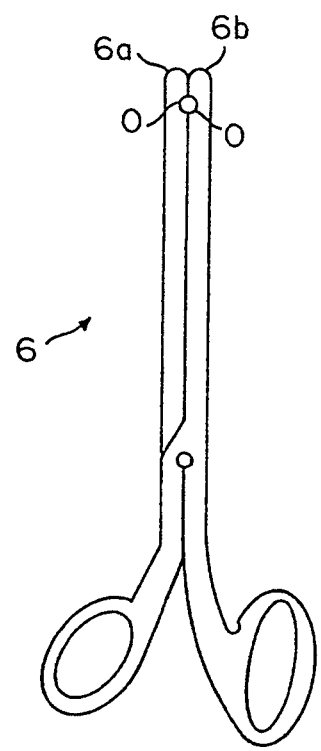
FIG. 12 is a plan view of a holder used by the surgeon to grasp the cannula and insert through the patient's palm; and, FIGS. 13A and 13B illustrate use of a surgical knife to cut a sheath about the tendon and release the trigger finger.

It will be understood that the forward end 1a of cannula 1 can be blunt and sized for ready insertion of one end of trocar 5 into this end of the cannula. Alternatively, and as shown in FIG. 7D, the forward end of a cannula 1' can be pointed or bullet tipped as indicated at 1a'. With this latter forward end configuration, a trocar is still used to insert the cannula through the palm. Rather, the forward end of the cannula is sharp enough to be easily inserted through the palm. In either embodiment, the other end 1b or 1b' of the cannula is blunt. Further, as shown in FIG. 12, cannula 1 or 1' is inserted through the palm using the holder 6. The holder has a clamp end with opposed jaws 6a, 6b in each of which is formed a semicircular opening O. The diameter of these openings generally conforms to the diameter of the cannula. This allows the surgeon to use the opposed handle end of the holder to grasp the cannula, insert the cannula through the palm, and then release the cannula. At the conclusion of the surgery, the surgeon again uses the holder to grasp the cannula and remove it from the patient's palm.

After completing insertion of the cannula through the palm, both ends 1a, 1b of the cannula are now extending out from the patient's hand. This is the condition shown in FIG. 8. If the surgeon used a cannula 1, he or she now removes the trocar from the one end of the cannula, being careful to leave the cannula in place. The surgeon then inserts an arthroscope 9 into one end of the cannula, and pushes the arthroscope forward through the cannula until it is adjacent the site of the constriction. Arthroscope 9 is comprised of a flexible bundle of fiber optic cables OC which are routed to a monitor 10. Use of the arthroscope allows the surgeon performing the method of the invention to view the surgical site. For this purpose, the surgeon feeds the fiber optic bundle through end 1b of the cannula until the forward end of the bundle is adjacent the area of the sheath or pulley which is to be cut. The surgeon views the site through the slot 2 in the cannula.

Figure 11:
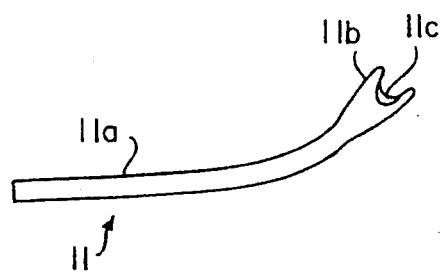
FIG. 11 illustrates a surgical knife of the invention which is inserted into the other end of the cannula and with which the surgeon can release the trigger finger.
Figure 13A:
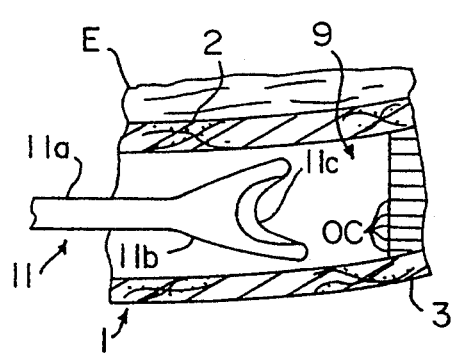

Next, the surgeon inserts a curved or flexible surgical knife 11 into the opposite end (end 1a) of the cannula. The surgeon pushes the knife forward into the cannula until it is immediately beneath the portion of the sheath or pulley to be cut in order to relieve the constriction on the tendon and release the trigger finger. As shown in FIG. 11, knife 11 has a shank portion 11a which can be grasped by the surgeon to manipulate the knife. For this purpose, the surgeon may use a holder similar to holder 6. That is, the holder has jaws with respective openings by which the shank of the knife can be grasped by the surgeon. The surgeon then moves the knife by manipulating the shank with the holder. Knife 11 also has an enlarged head 11b the thickness of which is narrower than the width of slot 2 in cannula 1. The height of the head is greater than the diameter of shank 11a; but, again, is less than the diameter of the cannula for the head to be insertable in the cannula. This is the condition shown in FIG. 13A.

Figure 13B:
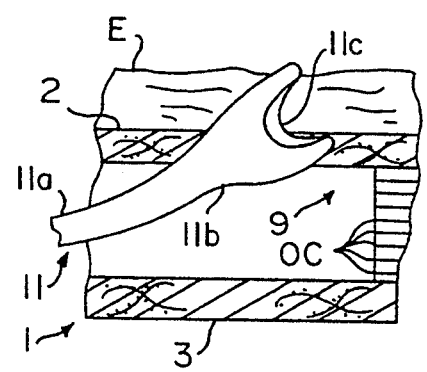

The head of the knife is widest at its outer end. The outer end of the knife has an inward or concave cutting edge 11c. The length of the cutting edge is shorter than the height of the knife at its outer end. This means the surgeon must rotate the knife through slot 2 in the cannula to bring the cutting edge to bear against the sheath. This is as shown in FIG. 13B.

Using the arthroscope to guide him or her, the surgeon proceeds to make the appropriate cuts in the pulley or sheath. This is done by the surgeon moving the cutting edge of the knife from its FIG. 13A to its FIG. 13B position and moving the knife through the slot in the cannula. As the cut or cuts are made in the annulus of covering material about the tendon, the restriction is relieved and the trigger finger released.

Figure 9:
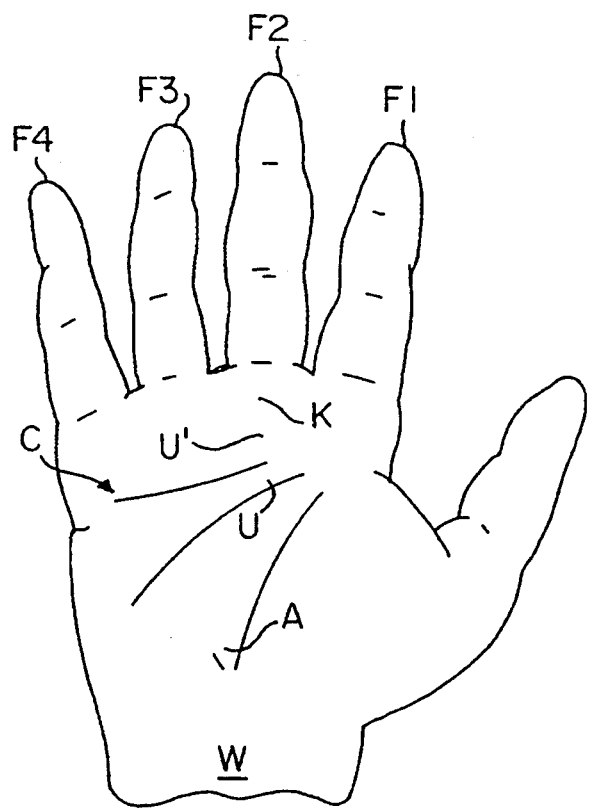
FIG. 9 is a view of the hand similar to FIG. 4 and illustrating its condition after the surgical procedure of the present invention is completed.
Figure 10:
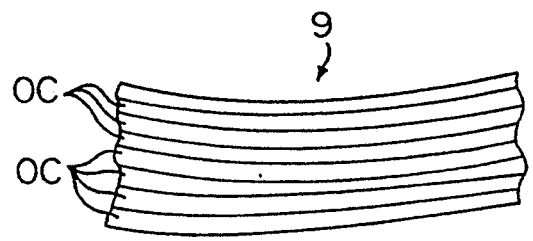
FIG. 10 represents an arthroscope inserted into one end of the cannula to enable a surgeon to view the surgical site.

When finished, the surgeon withdraws knife 11 from the one end of the cannula. He or she then withdraws arthroscope 9 from the other end. Next, the cannula is withdrawn from the patient's palm. One of the benefits of the surgical technique described is that because of the size of the cannula, puncture wounds U and U' do not require stitches to close them. And, as the puncture wounds heal, no scars are formed. Thus, as shown in FIG. 9, the holes U and U' made in the patient's hand are quite small compared with the incision I made as part of the conventional surgical procedure, and the resulting scar R seen in FIG. 4.

What has been described is a surgical method for use in relieving the trigger finger or trigger thumb condition of a patient. The procedure is an endoscopic surgical procedure. In performing the procedure a reference point is first located at the center of the thenar and lesser thenar muscles in the palm of the hand. After the routing of the flexor tendon going to each finger and thumb is determined using the reference point, an appropriate incision site is located. The skin is then punctured at first and second spaced sites. An endoscopic surgical instrument which is a curved, slotted cannula which may have an attached trocar is used to accomplish this. The cannula is left in place for use with a surgical knife by which the distal palm pulley causing the trigger finger is severed. An arthroscope is fitted in one end of the cannula to provide the surgeon a view of the surgical site. A surgical knife devised for use in this type surgery is inserted in the opposite end of the cannula and is used to make cuts in the sheath surrounding the constricted tendon to release the constriction. The punctures made in the palm of the hand by insertion of the cannula are sufficiently small that after completion of the surgery and removal of the cannula, no sutures are required to close the puncture holes. As healing takes place, no scars are formed in the palm of the hand. The endoscopic procedure can be performed by a surgeon as readily as previous surgical procedures used to effect similar repairs. Finally, the surgery can be performed at any convenient location such as the surgeon's office, a clinic, or a hospital and its performance only involves an attending physician and a surgical nurse or aide.

As various changes could be made in the above constructions without departing from the scope of the invention, it is intended that all matter contained in the above description or shown in the accompanying drawing shall be interpreted as illustrative and not in a limiting sense.

Having thus described the invention, what is claimed and desired to be secured by Letters Patent is:

1. A method of performing trigger finger release surgery comprising:

identifying a route of a flexor tendon through a palm of a hand to a finger or thumb of said hand suffering from a trigger finger condition, constriction of a protective sheath around said flexor tendon causing said trigger finger condition;

locating along an identified route a puncture site for insertion of a hollow surgical instrument into said palm;

inserting a leading end of said surgical instrument through a segment of skin covering the palm of said hand and pushing said leading end of said instrument back through said skin whereby a first puncture hole is made in said skin at an entry site and a second puncture hole at an exit site, said surgical instrument being inserted through said palm of said hand such that an insertion path of said instrument passes through said sheath;

leaving said surgical instrument in place and inserting therein a surgical knife by which said sheath can be cut to relieve said trigger finger condition;

cutting said sheath with said knife through an opening in said surgical instrument; and, withdrawing said knife and said surgical instrument from said palm, said surgical instrument being of a size such that after withdrawal of said instrument, said first and second puncture holes do not require stitches to close them, and, as said holes heal, no scars are formed.

2. The method of claim 1 wherein identifying said flexor tendon route includes locating a junction between a thenar muscle and a lesser thenar muscle at a base of said palm of said hand, locating a midpoint of a width of a pertinent finger at a base of said pertinent finger, and marking a straight line path between said junction and said midpoint.

3. The method of claim 2 wherein locating said puncture site includes identifying a location along said flexor tendon route where said straight line path crosses a distal crease formed in said palm of said hand.

4. The method of claim 3 wherein said surgical instrument is a curved cannula and inserting said instrument through said palm of said hand includes fitting a trocar in one end of said cannula and pushing said one end of said cannula through said palm of said hand along said path that includes said sheath of said flexor tendon.

5. The method of claim 4 wherein inserting said surgical instrument includes inserting a cannula having a diameter of 1.5 mm–2.5 mm.

6. The method of claim 4 further including removing said trocar from said one end of said cannula after insertion of said cannula through said palm.

7. The method of claim 6 wherein the step of inserting a surgical knife further includes inserting said surgical knife through said cannula after removal of said trocar and cutting through said flexor tendon sheath with said knife.

8. The method of claim 6 further including inserting a flexible arthroscope in an end of said cannula to allow a surgeon performing the trigger finger release surgery to view a surgical site where said sheath is to be cut.

9. The method of claim 8 wherein the step of inserting a surgical knife further includes inserting said surgical knife through an opposite end of said cannula to cut said sheath.

10. The method of claim 9 wherein withdrawing said surgical instrument from said palm first includes removing said flexible arthroscope and said surgical knife from said cannula, and then pulling said cannula back out of said palm along said path through which it was inserted.

11. In a method of performing trigger finger release surgery wherein a route of a flexor tendon through a palm of a hand to a finger or thumb of said hand suffering from trigger finger is identified, construction of a protective sheath around said flexor tendon causing a trigger finger condition, and a puncture site is located along said identified route for insertion of a surgical instrument into said palm, the improvement comprising;
   inserting a leading end of a hollow surgical instrument through a segment of skin covering said palm and pushing said leading end of said instrument back through said skin whereby a first puncture hole is made in said skin at an entry site and a second puncture hole is made at an exit site, said surgical instrument being pushed through said palm such that said surgical instrument passes through said sheath;
   leaving said hollow surgical instrument in place and inserting therein a surgical knife by which said sheath can be cut to relieve said trigger finger condition;
   cutting said sheath with said knife, said knife cutting said sheath through an opening in said surgical instrument; and,
   withdrawing said knife and said surgical instrument from said palm, said surgical instrument being of a size such that after withdrawal of said instrument, said first and second puncture holes do not require stitches to close them, and, as said holes heal, no scars are formed.

12. The method of claim 11 wherein said surgical instrument is a hollow, curved cannula and inserting the instrument through said palm of said hand includes fitting a trocar in one end of said cannula and pushing said end of the cannula through said palm of said hand along said path that includes said sheath of said flexor tendon.

13. The method of claim 12 wherein inserting said surgical instrument includes inserting a cannula having a diameter of 1.5 mm.—2.5 mm.

14. The method of claim 12 further including removing said trocar from said cannula after insertion of said cannula through said palm.

15. The method of claim 14 further including inserting a flexible arthroscope in an end of said cannula to allow a surgeon performing a trigger finger release surgery to view a surgical site where said sheath is to be cut.

16. The method of claim 15 wherein the step of inserting a surgical knife further includes inserting said surgical knife through an opposite end of said cannula to cut said sheath.

17. The method of claim 16 wherein withdrawing said surgical instrument from said palm first includes removing said flexible arthroscope and said surgical knife from said cannula, and then pulling said cannula back out of said palm along said path through which it was inserted.

18. A method of performing trigger finger release surgery comprising:
   identifying a route of a flexor tendon through a palm of a hand to a finger or thumb of said hand suffering from a trigger finger condition, constriction of a protective sheath around said flexor tendon causing said trigger finger condition;
   locating along said identified route a puncture site for insertion of a hollow surgical instrument into said palm;
   fitting a trocar in one end of a hollow, curved cannula and pushing said end of said cannula in which said trocar is fitted through a segment of skin covering said palm and back through said skin whereby a first puncture hole is made in said skin at an entry site and a second puncture hole at an exit site, said cannula being pushed through said palm such that the path of said instrument passes through said sheath;
   removing said trocar from said end of said cannula but leaving said cannula in place;
   inserting in one end of said cannula a flexible arthroscope by which a surgeon performing the surgery can view a surgical site;
   inserting in an opposite end of said cannula a surgical knife by which said sheath can be cut to relieve said trigger finger condition;
   cutting said sheath with said knife by extending a cutting edge of said knife through an opening in said cannula;
   withdrawing said knife and said arthroscope from said cannula; and,
   withdrawing said cannula from said palm, said cannula being of a size that after withdrawal of said cannula, said first and second puncture holes require no stitches to close them, and, as said holes heal, no scars are formed.

19. The method of claim 18 wherein identifying said flexor tendon route and locating said puncture site comprises:
   locating a junction between a thenar muscle and a lesser thenar muscle at a base of said palm, a midpoint of a width of a pertinent finger at a base of said finger, and marking a straight line path between said junction and said midpoint; and
   identifying a location along said flexor tendon route where said straight line path crosses a distal crease formed in said palm of said hand.

20. The method of claim 19 wherein pushing said cannula through said skin includes pushing a cannula having a diameter of 1.5 mm.—2.5 mm.

* * * * *